United States Patent [19]

Eckstein et al.

[11] Patent Number: 4,528,160
[45] Date of Patent: Jul. 9, 1985

[54] GAS DOSIMETER CONSTRUCTION

[75] Inventors: Wolfgang Eckstein, Sereetz; Kurt Leichnitz, Gross Gronau; Karl-Heinz Pannwitz, Lübeck; Horst Rabenecker, Stockelsdorf; Günter Wolff, Schwartau, all of Fed. Rep. of Germany

[73] Assignee: Drägerwerk Aktiengesellschaft, Fed. Rep. of Germany

[21] Appl. No.: 615,928

[22] Filed: May 31, 1984

[30] Foreign Application Priority Data

Jun. 14, 1983 [DE] Fed. Rep. of Germany ....... 3321356

[51] Int. Cl.³ .............................................. G01N 1/22
[52] U.S. Cl. ..................................... 422/86; 422/59; 422/88; 422/102; 422/104
[58] Field of Search .................. 73/23, 863.71, 864.01, 73/864.02, 864.72; 422/58–60, 85, 86, 83, 88, 102, 104

[56] References Cited

U.S. PATENT DOCUMENTS

| 3,474,003 | 10/1969 | Hirsch | 422/102 X |
| 3,507,623 | 4/1970 | McConnaughey | 422/86 |
| 3,626,762 | 12/1971 | Gilford | 422/102 X |
| 4,159,304 | 6/1979 | Shono | 422/59 X |
| 4,389,372 | 6/1983 | Lalin | 422/86 X |
| 4,481,297 | 11/1984 | Zucal et al. | 422/88 X |

FOREIGN PATENT DOCUMENTS

| 1075054 | 7/1967 | United Kingdom | 422/86 |
| 1075055 | 7/1967 | United Kingdom | 422/86 |

Primary Examiner—Robert Spitzer
Attorney, Agent, or Firm—McGlew and Tuttle

[57] ABSTRACT

A housing contains a diffusion indicator tube provided with a predetermined breaking point and the housing has an upper part and a lower part joined together by a film hinge. To open the inserted diffusion indicator tube its predetermined breaking point is positioned opposite the film hinge. By bending the housing parts, the break-off end breaks off the test tube at the predetermined breaking point, thereby opening the reaction section. The parts of the test tube are removed, and then the reaction section is pushed into the upper part, now with its closed end first, whereupon it is snapped into the lower part. Its opening at the bottom shoulder of the lower part is exposed to the ambient atmosphere which diffuses into it. In the presence of the gas to be monitored there will be discoloration due to reaction. The discoloration can be observed continuously through the open side of the holding means.

7 Claims, 4 Drawing Figures

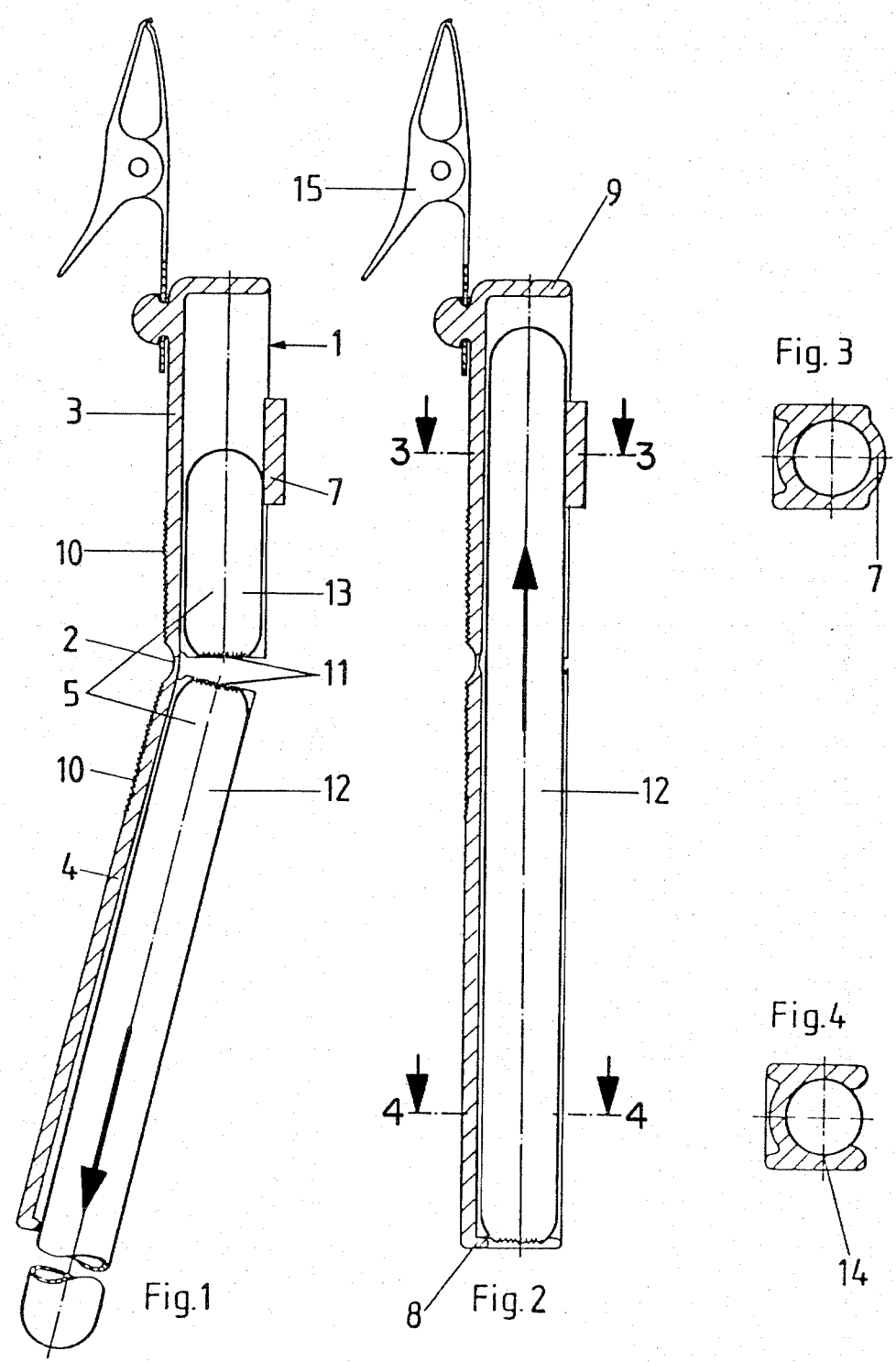

GAS DOSIMETER CONSTRUCTION

FIELD AND BACKGROUND OF THE INVENTION

The invention relates particularly to a gas dosimeter in a holding means with a clip for fastening to the user's clothes, containing a diffusion indicator tube with a predetermined breaking point for opening.

By means of the gas dosimeter, diffusion test or indicator tubes are brought into contact with the ambient atmosphere. The test air is not transported into the test tube by a transporting means such as a pump, but automatically by diffusion. The discoloration in the indicator tube, in conjunction with the testing period, is then a measure of the concentration of the gas to be detected.

One know colorimetric gas dosimeter contains a dosimeter tube disposed in a transparent retaining tube. The dosimeter tube, with a color indicator for the gas to be detected, is fused shut at both ends when shipped by the factory. To open it, it has a break line in the vicinity of one end. The larger, transparent retaining tube is made of an unbreakable plastic. At one open end it has a clip for fastening it to the user's clothes. The other end can be closed by an elastic stopper having an axial recess in which the end remote from the break line of the dosimeter or indicator tube is received.

Prior to use, the receiving stopper with the dosimeter tube are withdrawn from the retaining tube, the free ends of the dosimeter tube are broken off at the break line and, in an open state, it is again inserted into the retaining tube. The color indicator then protrudes over the opening of the dosimeter tube, and the open end of the retaining tube communicates with the ambient air so that the gas to be detected can diffuse therein. The coloration is a measure of the absorbed amount (German OS No. 31 367 756).

To avoid possible injuries from glass splinters, hands and face must be protected. This makes the use difficult or, under careless handling, even dangerous (MSA Dosimeter Tubes, Instructions for Detecting Nitrogen Dioxide using Nitrogen Dioxide Dosimeter, part No. 469414).

SUMMARY OF THE INVENTION

The invention is directed to a gas dosimeter or detector tube which is received in a holder and comprises a diffusion-type indicator tube, which is simple and safe to handle and makes sure that while breaking open the indicator tube, the user is protected against flying splinters, and the tube is protected from being broken during the period of measuring, and the reading is ensured.

In accordance with the invention, this is obtained by providing that the holding means, comprising a housing having an upper part and a lower part joined to each other by a film hinge, accommodates a diffusion indicator tube. The indicator tube is divided by a predetermined breaking point into a reaction section and a break-off end.

Prior to being used, the film hinge and the predetermined breaking point are disposed opposite each other for breaking. The reaction section is retained in the lower part, and the closed break-off end of the tube is retained in the upper part.

In further development, the upper part and the lower part have gripping corrugations next to the film hinge joining them; furthermore, the receptacle is closed off in the upper part by an encircling yoke radially and by a wall or closure axially. The lower part contains a shoulder at a lower entry. The inside length of the upper part from the closure to the film hinge and the length of the breakoff end are advantageously the same.

An advantage obtained by the invention, in particular, is that the holding means is practically made of one part and in one operation and it makes it possible to break open the diffusion indicator tube for use without any danger to the user. No goggles for eye protection against flying splinters are needed. The open receptacle for the diffusion test tube allows it to be observed unobstructedly to determine the gas concentration. A concentration determination perhaps made difficult by scratched retaining materials which are otherwise transparent cannot occur.

The section of the holding means assures great stability, thereby protecting the test tubes against breakage.

Accordingly an object of the invention is to provide a gas dosimeter which comprises an outer housing having first and second parts which are joined together by a hinge and constructed to hold a transparent indicator tube therein which is initially closed at each end and which has a break point intermediate its length positioned adjacent the hinge so that when the housing parts are pivoted about the hinge the indicator tube is broken into a reaction section which remains in the second part of the housing on one side of the break point and a remaining section which remains in the first part of the housing and which may be moved, the second part being opened by the breaking so as to permit the ambient atmosphere to diffuse into it and give an indication of the gas which is present in the atmosphere.

A further object of the invention is to provide a dosimeter which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a sectional view of a dosimeter constructed in accordance with the invention and shown in a position in which the indicator tube contained in the housing is opened by bending the housing parts about its hinge and constructed in accordance with the invention;

FIG. 2 is a view of the dosimeter tube with the opened reaction section of the indicator tube reversed in the housing and with its opened end oriented to permit gas to diffuse into the indicator tube from the bottom thereof;

FIG. 3 is a section taken along the line A—A of FIG. 2; and

FIG. 4 is a section taken along the line B—B of FIG. 2.

GENERAL DESCRIPTION OF PREFERRED EMBODIMENTS

Referring to the drawings in particular the invention embodied therein comprises holding means or housing generally designated 1 having a first or upper part 3 and a second or lower part 4 which are hinged together by a film hinge 2 so that the housing may be integrally formed. A transparent indicator tube generally designed 5 is arranged in the housing 1 in an initial position with both ends of the indicator tube 5 closed. Break point 11 is formed intermediate the length of the indicator tube 5 and it is positioned adjacent the hinge 2 so that the housing parts which are strong enough when they are pivoted relative to each other will effect the breaking of the indicator tube 5. To facilitate the breaking the upper part 3 of the housing 1 is advantageously formed with a yoke 7 or a closing portion which grasps the breakoff end or remaining end 13 of the tube 5 to open the reaction section 12 of the tube 5.

In accordance with a feature of the invention the lower part 4 of the housing 1 is provided with a shoulder for retaining edge 8 which holds the open reaction section in the housing after it is reversed so that its closed end is uppermost and this positions the lower or opened end so that the interior of the reaction section 12 is open for the inflow of the atmospheric air therein.

The dosimeter includes holding means 1 having an upper part 3 and a lower part 4, joined to each other by the film hinge 2. The holding means 1 accommodates a diffusion test or indicator tube 5 therein. The holding means 1, made of a plastic such as polyethylene or polypropylene, provides open receptacle 14 of a closed and open cross-section according to FIGS. 3 and 4. The upper part is closed by a yoke 7 advantageously provided for the breaking operation. The test tube is supported against falling out by an undercut in a radial direction and by a shoulder 8 in axial direction at the open end of the lower part 4. The same is achieved in the upper part 3 by a closure 9. Also fastened there is the clip 15 needed to fasten the dosimeter to the user's clothes. Next to the film hinge 2, the upper part 3 and the lower part 4 have gripping corrugations 10 to prevent the fingers from slipping during the breaking operation. The diffusion test tube 5 with the color indicator for the gas to be detected in the reaction section 12 contains, at the test gas entry end, the break-off end 13, divided by a predetermined breaking point 11.

Handling the dosimeter is simple. To use it, the break-off end 13 of the diffusion indicator tube 5 is introduced into the upper part 3 of the holding means 1 under the yoke 7 until the predetermined breaking point 11 is opposite the film hinge 2, and the reaction section 12 is then snapped into the lower part 4. Gripping the corrugations 10 with the thumbs of both hands and the diffusion indicator tube 5 with the other fingers, the holding means 1 is bent in the film hinge 2 and the diffusion indicator tube 5 broken. In this process, the open side of the receptacle 14 should face away from the body.

Breakoff end 13 and reaction section 12 are removed from the holding means 1, and the then still closed end of the reaction section 12 is then pushed under the yoke 7 again and snapped into the lower part 4. The shoulder 8 prevents the reaction section 12 from sliding out of the holding means 1.

While specific embodiments of the invention have been shown and described in detail to illustrate the application of the principles of the invention, it will be understood that the invention may be embodied otherwise without departing from such principles.

What is claimed is:

1. A gas dosimeter, comprising an outer housing of first and second parts joined together by a hinge, a transparent indicator tube in said housing being initially closed at each end and having a breakpoint intermediate its length positioned adjacent said hinge with a reaction section of said indicator tube being in said second part of said housing on one side of said breakpoint and the remaining breakoff part being in said housing first part, said housing first and second parts being pivotable about said hinge to break said indicator tube along said break point to open said reaction section, said reaction section being retainable in said housing after being opened to permit the ambient atmosphere to diffuse into said reaction section.

2. A gas dosimeter according to claim 1, wherein said housing first and second parts have gripping corrugations thereon on the exterior next to said hinge.

3. A gas dosimeter according to claim 1, wherein said housing first part is closed at its end and including a yoke portion of said first part circling said indicator tube, said second part having a shoulder forming a supporting ledge adjacent its end.

4. A gas dosimeter according to claim 1, wherein said housing first part has a length from the end thereof to said hinge which is equal to the length of said indicator tube from an end thereof to said break point.

5. A gas dosimeter according to claim 1, wherein said housing includes side wall portion between which said transparent indicator tube is engageable, said first housing part including a yoke portion extending between said side wall portions.

6. A gas dosimeter according to claim 5, wherein said first housing part has a closed end with said second housing part having an end with a ledge formed thereon, said yoke being located so that initially said indicator tube may extend beyond said ledge with one end thereof being located within said yoke.

7. A gas dosimeter according to claim 1, including a securing clip connected to said housing.

* * * * *